United States Patent [19]

Ezzell et al.

[11] Patent Number: 4,687,821
[45] Date of Patent: Aug. 18, 1987

[54] PREPARATION, DECARBOXYLATION AND POLYMERIZATION OF NOVEL ACID FLUORIDES AND RESULTING MONOMERS

[75] Inventors: Bobby R. Ezzell, Lake Jackson; William P. Carl, Angleton; William A. Mod, Lake Jackson, all of Tex.

[73] Assignee: The Dow Chemical Company, Midland, Mich.

[21] Appl. No.: 510,517

[22] Filed: Jul. 5, 1983

Related U.S. Application Data

[62] Division of Ser. No. 158,426, Jun. 11, 1980, Pat. No. 4,515,989.

[51] Int. Cl.$^4$ .............................................. C08F 14/18
[52] U.S. Cl. ................................... 526/247; 528/392; 528/401
[58] Field of Search ................. 526/247; 528/392, 401

[56] References Cited

U.S. PATENT DOCUMENTS

| | | | |
|---|---|---|---|
| 3,450,684 | 6/1969 | Darby | 526/247 |
| 3,896,179 | 7/1975 | Resnick | 526/247 |
| 4,330,654 | 5/1982 | Ezzell et al. | 526/247 |

Primary Examiner—Paul R. Michl

[57] ABSTRACT

Compounds represented by the general formulas

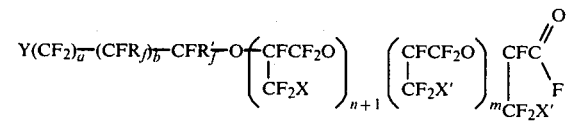

are prepared by reacting halofluoropropylene oxides with fluorinated acid fluorides and ketones.

9 Claims, No Drawings

PREPARATION, DECARBOXYLATION AND POLYMERIZATION OF NOVEL ACID FLUORIDES AND RESULTING MONOMERS

This is a divisional of application Ser. No. 158,426, filed June 11, 1980, now U.S. Pat. No. 4,515,989.

BACKGROUND OF THE INVENTION

U.S. Pat. No. 3,536,733 teaches the preparation of compounds represented by the general formula

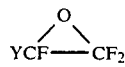

where Y is F or $CF_3$.

U.S. Pat. Nos. 3,214,478 and 3,242,218 teach a process for preparing compounds having the general formula

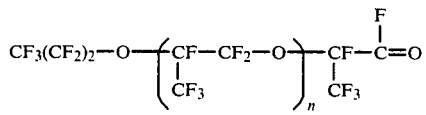

where n is 0 or an integer greater than 0.

U.S. Pat. No. 3,250,806 teaches fluorocarbons having the general formula

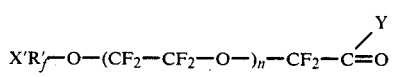

where
n = 0 to 20;
$R_f'$ = perfluoroalkylene radical
COY is a carboxylic acid group or a carboxylic acid fluoride; and
X' is halogen or hydrogen.

German Pat. No. 1,238,458 teaches the reaction of iodo substituted perfluorocarboxylic acid fluorides with hexafluoropropylene oxide to make acid fluoride intermediates which can be pyrolyzed in the presence of an inorganic compound such as ZnO to produce vinyl ether compounds. The vinyl ether products, when copolymerized with tetrafluoroethylene form melt processable polymers that can be crosslinked by thermal decomposition of the perfluoro alkyl iodide.

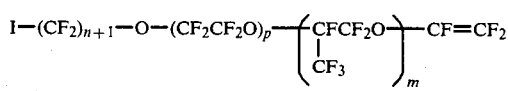

where
n = 1-8
p = 0-5
m = 0-5

A specific example being

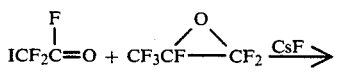

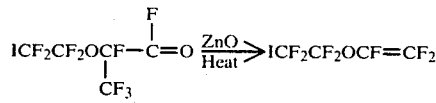

U.S. Pat. No. 3,450,684 teaches the preparation of vinyl ethers by reacting an acid fluoride with hexafluoropropylene oxide followed by decarboxylation using an activator such as ZnO or silica according to the following reactions:

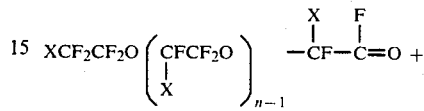

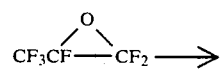

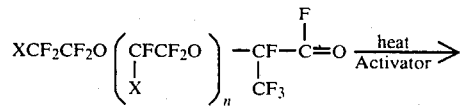

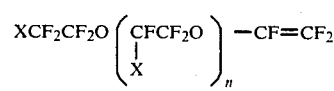

where
X is F, Cl, H, $CH_3$, $CF_2Cl$ or $CF_3$
n is at least 1.

Copolymerization of these monomers with tetrafluoroethylene forms polymers having lower melt viscosity than the parent tetrafluoroethylene polymer.

U.S. Pat. No. 3,114,778 teaches the formation of vinyl ethers by reacting an acid fluoride with hexafluoropropylene oxide to produce an intermediate compound which may be decarboxylated to a vinyl ether according to the following reactions:

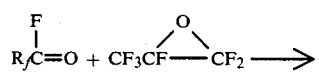

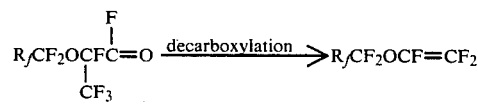

where $R_f$ is, for example, a perfluoroalkyl radical. Homopolymers and copolymers, with tetrafluoroethylene, of the vinyl ethers is taught.

Fern, et al, Journal of Polymer Science: Part A-1, Vol. 4, 131–140 (1966) discloses that in the pyrolysis of sodium salts of carboxylic acids which contain fluorine and chlorine in the beta position, sodium chloride is preferentially, but not exclusively eliminated. For example:

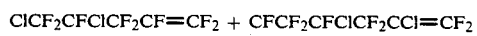

U.S. Pat. No. 3,282,875 shows decarboxylation of intermediates to form various vinyl ethers. At higher temperatures of around 300° C., vinyl ether yields of about 80% were obtained. When, however, lower temperatures of about 200° C. were used to decarboxylate, yields of about 20-30% were obtained.

R. D. Chambers, in his book, *Fluorine in Organic Chemistry*, published by John Wiley & Sons, 1973, pages 211-212, teaches that carboxylic acid derivatives may be converted to olefins. The conversion involves the loss of carbon dioxide and forms an intermediate carbanion. The intermediate then looses NaF to form the resulting olefin.

Evans et al., in the *Journal of Organic Chemistry* Volume 33, page 1838, (1968) describes catalysts useful for the reaction between acid fluorides and epoxides.

M. Hudlicky in *Chemistry of Organic Fluorine Compounds—2nd Edition*, John Wiley & Sons, New York, pages 20-21, teaches the well-known reaction between tetrafluoroethylene and perfluoroalkyl iodides to form telomeric perfluoroalkyl iodides according to the following reaction:

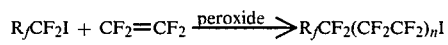

Various methods for polymerization are taught in the following references: *Emulsion Polymerization—Theory and Practice* by D. C. Blackley, John Wiley & Sons; U.S. Pat. Nos. 3,041,317; 2,393,967; 2,559,752; and 2,593,583.

BRIEF DESCRIPTION OF THE INVENTION

Novel compounds represented by the general formula

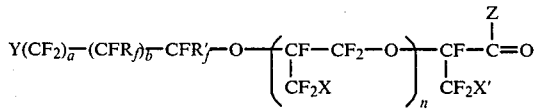

are prepared by reacting fluorinated epoxides of the general structures

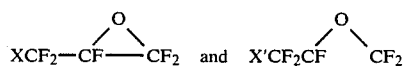

with compounds of the formula

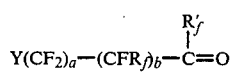

for a time and a temperature sufficient to produce said compounds: where
 a=is to 3;
 b=is to 3;
 n=is 0 or an integer greater than 0;
 $R_f'$ and $R_f$ are independently selected from the group consisting of F, Cl, perfluoroalkyl and fluorochloroalkyl;
 X=F, Cl Br or mixtures thereof when n>1;
 X'=Cl or Br;
 Y is a halogen such as Cl, Br, I or F;
 Z=F, Cl, Br, OH, NRR' or OA;

R and R' are independently selected from the group consisting of hydrogen, or an alkyl having one or more than one carbon atom and aryl; and
 A=alkali metal, quaternary nitrogen, or R.

These carboxylic acids or derivatives are easily converted to vinyl ether monomers by the methods of the prior art such as pyrolysis with activators such as ZnO or silica, but preferentially and unexpectedly under milder conditions and in extremely high yield by simple reaction with sodium carbonate.

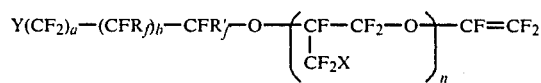

where Y, a, b, n, $R_f$, $R_f'$ and X are defined above.

The above compounds may also be prepared according to the following reaction:

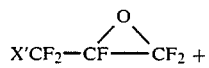

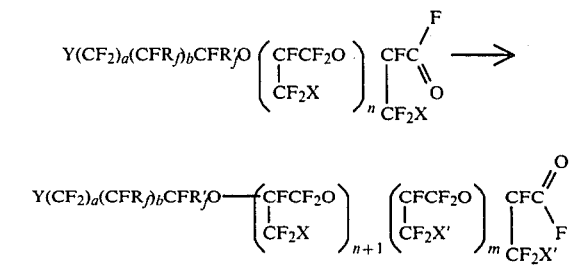

where
 a=is to 3;
 b=is to 3;
 n=0 or an integer greater than 0;
 m=0 or an integer greater than 0;
 $R_f'$ and $R_f$ are independently selected from the group consisting of F, Cl, perfluoroalkyl radicals and fluorochloroalkyl radicals;
 X=F, Cl or Br or mixtures thereof when n>0;
 X' is independently Cl or Br.
 Y=I, F, Cl, or Br.

These compounds may be decarboxylated to form vinyl ethers represented by the general formula

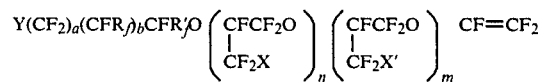

where m, n, Y, a, b, $R_f$, $R_f'$, X and X' are defined above.

Polymers, made from the vinyl ethers of the present invention are useful plastic materials. When copolymerized with vinyl monomers, such as tetrafluoroethylene, simpler melt processability results and a potential reactive site is introduced into the polymers.

DETAILED DESCRIPTION OF THE INVENTION

The present invention relates to a novel class of fluorine containing ethers and methods for their preparation which ethers have terminal functionality according to the general formula:

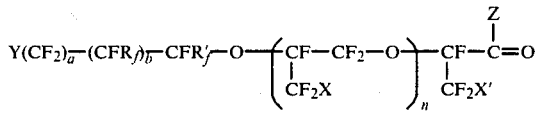

wherein
- a = is to 3;
- b = is to 3;
- n = 0 or an integer greater than 0;
- $R_f'$ and $R_f$ are independently selected from the group consisting of F, Cl, perfluoroalkyl and fluorochloroalkyl;
- X = F, Cl or Br or mixtures thereof when n > 1;
- X' = Cl or Br or mixtures thereof;
- Y is a halogen such as Cl, Br, I or F;
- Z = F, Cl, Br, OH, NRR' or OA;
- R and R' are independently selected from the group consisting of hydrogen, an alkyl having one or more than one carbon atom and aryl; and
- A = alkali metal, quaternary nitrogen, or R.

These compounds are intermediates which may be further reacted to form vinyl ether monomers

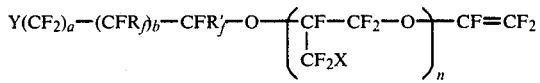

where Y, a, b, n, $R_f$, $R_f'$ and X are defined above.

These monomers are useful for forming chemically stable plastic materials and as modifiers for various fluorocarbon polymers. Any one monomer represented by the immediately preceding general formula may be homopolymerized with itself or any one monomer may be copolymerized with any other monomer represented by the general formula. Additionally, more than two kinds of monomers represented by the general formula may be copolymerized.

In addition, any one or more of the monomers represented by the general formula may be copolymerized with any one or more of the monomers selected from the group consisting of tetrafluoroethylene, trifluoromonochlorethylene, trifluoroethylene, vinylidene fluoride, 1,1-difluoro-2,2-dichloroethylene, 1,1-difluoro-2-chloroethylene, hexafluoropropylene, 1,1,1,3,3-pentafluoropropylene, octafluoroisobutylene, ethylene, vinyl chloride, and alkyl vinyl ether.

For example, when Y = Cl, Br, F or I, the monomer

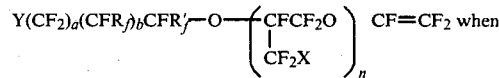

incorporated (by copolymerization) into polymers of well known monomers such as tetrafluoroethylene, chlorotrifluoroethylene or the like, impart useful properties. The copolymers are lower melting, thus facilitating fabrication. This property becomes extremely important in the case where the parent polymer is derived from tetrafluoroethylene. It would be difficult, if not impossible, to fabricate the polymer by conventional means such as melt extrusion without incorporation of a second component such as the above monomer. In addition to modifying physical properties, incorporating monomers derived from the intermediates where Y = Cl or Br in polymers of tetrafluoroethylene can be useful for introducing a site for further reaction of the polymers either before or after the fabrication, but preferably after. It is well known that perfluoropolymers such as Teflon ® are for most practical purposes inert. Only extreme reaction conditions such as reaction with sodium vapor affect their chemical integrity. Introduction of controlled amounts of the present monomers results in the polymers having a group more chemically reactive than is the case with the perfluoropolymers. Reaction with strong bases such as alkyl alkali metals can lead to intermediates useful for chemical modification such as introducing sulfonate groups for wettability of the polymers. In addition to the above uses, addition of a monomer derived from the present invention to copolymers of monomers having ion exchange functionality and tetrafluoroethylene to form terpolymers, for example when Y = Cl, that have

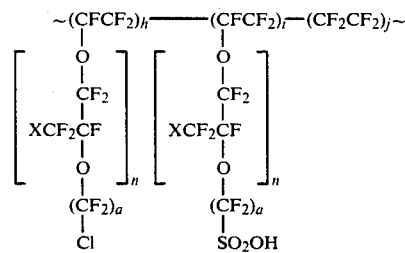

superior electrical properties compared to the copolymers alone when used as ion exchange membranes in chlor-alkali cells.

The radical X is chosen from the halogens Cl, Br or F, while X' is chosen from Cl or Br. While iodine would also be a useful radical for X or X', formation of the ethers by the chemistry taught herein is hampered by side reactions causing low or non-existant yields to the desired compounds.

The intermediate compounds of the present invention are conveniently prepared by reacting an acylfluoride or ketone of the general formula

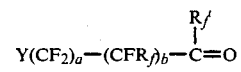

with a perhalofluoro propylene epoxide of the formula

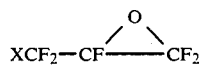

where Y, $R_f$, $R_f'$, and X are as defined above, the reactions are done in the presence of a fluoride ion yielding compound (MF-catalyst) at from below about $-20°$ C. to above about 50° C., in the liquid state, desirably in a liquid solvent for the intermediate fluoroalkoxide $Y(CF_2)_a$—$(CFR_f)_b$—$CFR_f'O^-M^+$ formed between the acid fluoride or ketone

and the metal or ammonium fluoride ion yielding catalyst (MF). The reactions proceed generally according to the equation

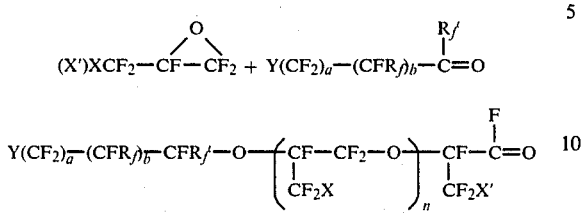

where
a = to 3;
b = to 3;
n = 0 or an interger greater than 0;
$R_f'$ and $R_f$ are independently selected from the group consisting of F, Cl, perfluoroalkyl and fluorochloroalkyl;
X = F, Cl, Br or mixtures thereof when n > 1;
X' = Cl or Br;
Y = I, Br, Cl or F In the special case where a = 2, b = 0, $R_f' = F$, Y = X = X' = Cl or Br, and Z = F the reaction can be done in either one or two steps. In this case, the first reaction of the fluoride ion is with the halofluoropropylene oxide compound rather than with the carbonyl of the substituted fluorocarbon acid fluoride. A fluorocarbon alkoxide is produced by this reaction which can either react with additional epoxide or lose fluoride ion to produce an acid fluoride.

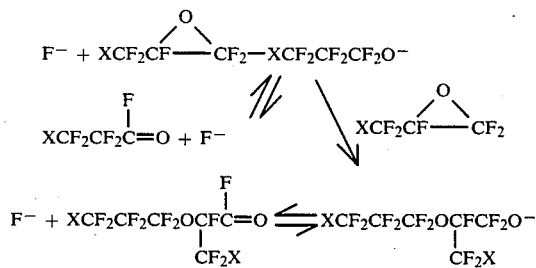

As can be seen from the above scheme, it is possible to rearrange the epoxide to acid fluoride with fluoride ion and then use the acid fluoride as demonstrated by the general scheme or one can simply react the epoxide in the presence of fluoride ion in a single step without isolation of the intermediate acid fluoride.

Conversion of acid halides such as the acid fluorides described herein to carboxylic acids and derivatives by reaction with nucleophiles are well known to those skilled in the art. For example, conversion of the acid fluoride to the corresponding carboxylic acid is easily accomplished by reaction with water. Conversion to esters or amides is accomplished by reaction with alcohols or amines, respectively. The carboxylic acid intermediates (Z = OH) are easily converted to acid chlorides and bromides (Z = Cl, Br) by reaction with appropriate halogenation agents such as $PCl_5$ and $PBr_5$.

Optional, additional reactions of the carboxylic acid fluorides proceed according to the following equation:

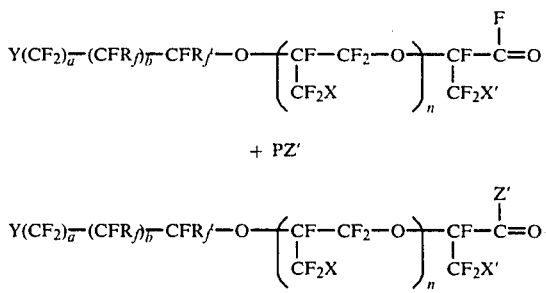

where
a = is to 3;
b = is to 3;
n = is 0 or an interger greater than 0;
$R_f'$ and $R_f$ are independently selected from the group consisting of F, Cl, perfluoroalkyl and fluorochloroalkyl;
X = F, Cl, Br or mixtures thereof when n > 1;
X' = Cl or Br;
Y is I, Br, Cl or F;
Z' = OH, NRR' or OR;
R and R' are independently selected from the group consisting of hydrogen, an alkyl having one or more than one carbon atom and aryl; and
P is a cation or capable of forming a cation, such as $Na^+$, $K^+$, $H^+$, etc.

It is of course to be understood that the ratio of reactants, the temperature of reaction, the amount of catalyst, as well as the amount and kind of solvent, influence the course, speed and direction of the reaction. Naturally the ratio of reactants bears more directly on the value of n in the generic formula than the other factors noted. For example, employing 1 or more moles of acid halide compound per mole of perhalofluro epoxide results in a product rich in the n = 0 product, i.e., greater than 1.5 n = 0 to n = 1, respectively and if the ratio is 2 to 1, respectively, the n = 0 product, respectively, is about 92 to 1, respectively, whereas employing greater than 1 mole epoxide compound per mole of acid fluoride compound, i.e., 2 to 1, respectively, results in a product having a 3:9:1 ratio of n = 2:n = 1:n = 0 products. The ratio of reactants thus can range, for practical purposes, from about 2 to 3 moles of the acylfluoride per mole of the halofluoro epoxide to 1 to 20 moles of the epoxide per mole of the acyl fluoride, the high acyl fluoride to epoxide producing predominantly the n = 0 and the high epoxide to acyl fluoride producing the n = 2–12 ether, respectively, and mixtures thereof.

Solvents employed in accordance with the present invention should be nonreactive (i.e., do not contain hydroxyl groups) and have at least a solubility for the reactants and the intermediate fluoroalkoxide formed between the acyl fluoride or ketone compound and the catalyst. Whether or not the products are significantly soluble in the solvent is a matter of choice and can be used as a controlling factor for selectively controlling the n value in the final product. For example, if a high n value is desired, it is advantageous that the product having at least n = 0 to 1 be soluble in the solvent to give the intermediates (n = 0 and n = 1) time to react to produce the final n = 1, 2 or higher product. In addition, the amount of solvent can be adjusted to accomplish somewhat similar results. Suitable solvents which may be employed to take advantage of the solubility plus amount factor are tetraglyme, diglyme, glyme, acetonitrile, nitrobenzene and the like. Exemplary of a preferred solvent is tetraglyme which has a suitable solvency for the intermediate.

Substantially any fluoride ionizable at the reaction temperatures may be used as a catalyst, however, CsF and KF are the most preferred but AgF, tetra alkyl ammonium fluoride as well as others listed in Evans, et al., *J. Org. Chem.* 33 1837 (1968) may be employed with satisfactory results.

The temperature of the reaction also effectuates a controlling factor on the end product obtained. For example, low temperatures such as $-20°$ C. favor $n=0$ products and higher temperatures, $50°$ C. and above, favor higher n values.

It has been discovered that the intermediates discussed above decarboxylate under far milder conditions and in excellent yields compared to those of the prior art

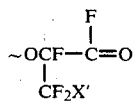

where $X'=Br, Cl$ as opposed to $X'=F$.

It has repeatedly been taught that preferential methods for the decarboxylation of compounds where $X'=F$ involve pyrolysis with activators such as ZnO at temperatures between $300°$ and $600°$ C. While it is taught that these reactions do proceed at lower temperatures with some bases, these methods are generally inferior to the high temperature methods because of lower yields (U.S. Pat. No. 3,282,875). While the intermediates of the present invention decarboxylate readily by the extreme conditions reported in the prior art, such conditions are neither required or desirable. These intermediates decarboxylate in near quantitative yields to the desired vinyl ether monomers at conditions as mild as a suspension of sodium carbonate in a solvent and temperatures at or below $100°$ C.

In addition to the ease of reaction as discussed above, the near quantitative yield to only the fluorine substituted olefin group is surprising. It is generally accepted that conversion of carboxylic acid derivatives to olefins involves loss of carbon dioxide to form an intermediate carbanion. In the present invention, this reaction could conceivably produce the intermediate shown below.

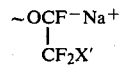

where $X'=Cl$ or $Br$
This intermediate then loses $NaX'$ to form the resulting olefin.

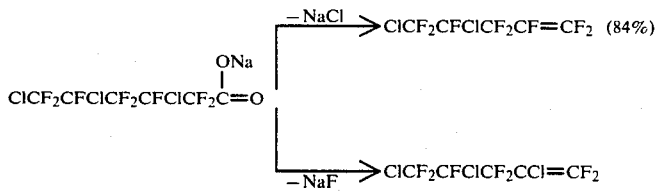

In this intermediate, it is possible to eliminate either $NaX'$ or $NaF$. Elimination of $NaF$ would result in another olefin, $\sim OCF=CFX'$, which would not be particularly useful for subsequent polymerization reactions and would thus require a tedious purification procedure for its removal. While it is not particularly surprising that loss of $NaX'$ predominates in the reaction, it is surprising that loss of $NaX'$, particularly when $X'=Cl$, as opposed to $NaF$ is the sole detected course of the reaction. As discussed previously, Fearn reports that elimination of both F and Cl occur in the following pyrolysis, though elimination of NaCl predominates.

$$ClCF_2CFClCF_2CFClCF_2\overset{ONa}{C}=O \begin{array}{c} \xrightarrow{-NaCl} ClCF_2CFClCF_2CF=CF_2 \ (84\%) \\ \\ \xrightarrow{-NaF} ClCF_2CFClCF_2CCl=CF_2 \end{array}$$

Analytical results from I.R., vpc-mass spectrometer and $F^{19}$ NMR have shown no evidence of a second vinyl ether (namely $\sim OCF=CFCl$) component in the olefins prepared by decarboxylation of the acid fluoride intermediates of the present invention.

In general, the polymerization procedures and techniques followed in the present invention are known. A very good reference for polymerization techniques is *Emulsion Polymerization—Theory and Practice*, by D. C. Blackley, published by John Wiley & Sons.

Additionally, the copolymer used in the present invention may be prepared by general polymerization techniques developed for homo- and copolymerizations of fluorinated ethylenes, particularly those employed for tetrafluoroethylene which are described in the literature. Non-aqueous techniques for preparing the copolymers of the present invention include that of U.S. Pat. No. 3,041,317, to H. H. Gibbs, et al, that is by the polymerization of a mixture of the major monomer therein, such as tetrafluoroethylene, and a fluorinated ethylene containing sulfonyl fluoride in the presence of a free radical initiator, preferably a perfluorocarbon peroxide or azo compound, at a temperature in the range $0°-200°$ C. and at pressures in the range 1–200 atmospheres, or more. The non-aqueous polymerization may, if desired, be carried out in the presence of a fluorinated solvent. Suitable fluorinated solvents are inert, liquid, perfluorinated hydrocarbons, such as perfluoromethylcyclohexane, perfluorodimethylcyclobutane, perfluorooctane, perfluorobenzene and the like.

Aqueous techniques which may also be used for preparing the copolymer used in this invention include contacting the monomers with an aqueous medium containing a free-radical initiator to obtain a slurry of polymer particles in non-waterwet or granular form, as disclosed in U.S. Pat. No. 2,393,967 to Brubaker or contacting the monomers with an aqueous medium containing both a free-radical initiator and a technologically inactive dispersing agent, to obtain an aqueous colloidal dispersion of polymer particles and coagulating the dispersion, as disclosed, for example, in U.S. Pat.

No. 2,559,752 to Berry and U.S. Pat. No. 2,593,583 to Lontz.

It is particularly beneficial to form polymers from the vinyl ether monomers of the present invention where Y=Cl and Br and not iodine. It is well known, M. Hudlicky, Chemistry of Organic Fluorine Compounds, 2nd Edition, John Wiley & Sons, New York, pages 420–421, that perfluoroalkyl iodides react under mild conditions with fluorovinyl compounds, such as tetrafluoroethylene, to form telomeric perfluoroalkyl iodides.

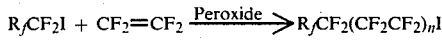

This reaction can be iniated with either peroxide compounds or heat. The prior art teaches copolymers of tetrafluoroethylene and iodoperfluoroalkyl vinyl ethers as useful since on heating they lose iodine and form crosslinked fluorocarbon resins. Formation of high molecular weight, linear polymers from iodo substituted monomers is severely restricted, at best, because of competing reactions of the alkyl iodide moiety with the olefinic moiety entering into the polymerization reaction. At least, highly branched, low molecular weight polymeric materials can be formed using conventional polymerization techniques. Formation of strong flexible films or structural materials, from the polymers, usually associated with high molecular weight plastic materials, would be essentially eliminated.

Peroxide or heat iniated reactions of perfluoroalkyl chlorides or bromides, particularly chlorides, with olefins does not take place nearly as readily as perfluoroalkyl iodides. In fact, fluorochloro compounds are not known to take part, via the chloro substituent, in this reaction. Thus, it is possible, using the vinyl ether monomers of the present invention, to form high molecular weight, plastic type materials by copolymerizing with other vinyl monomers, such as tetrafluoroethylene, by conventional polymerization techniques known for producing fluoropolymers. The resulting polymers have the added feature of having a reaction site (Y), known to be more reactive than perfluoropolymers where any additional reaction would have to take part on a fluoro substituent. Only few reactions and these requiring extreme conditions are known to take place at a C-F linkage. In fact, the non reactivity of this linkage accounts for the commercial significance of known fluoropolymers. Fluorocompounds having Cl, Br, and I substituents are known to take part in metallation reactions with such metallating reagents as alkyl alkali metals to produce reactive intermediates that undergo a variety of reactions.

EXAMPLE 1

50 ml dry tetraglyme and 8.35 g CsF were added to a 100 ml 3-neck flask equipped with a stirrer, thermometer, $-78°$ C. reflux condenser and an inlet port. Two $-78°$ C. traps in series were connected downstream of the reflux condenser. A slight back pressure was maintained on the system with dry $N_2$. The tetraglyme and CsF were mixed for 45 min. to 1 hour. The reactor was cooled to 0° C. to 10° C. and 7.26 g ClCF$_2$COF was added slowly through the inlet port, controlled to barely observed condensation on the reflux condenser. The mixture was stirred for 1 hour at room temperature. Ten grams of

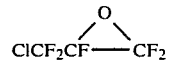

were added to the mixture limiting the addition by observing the reflux off the condenser. The mixture was allowed to stir for an hour. The product which separated as a bottom layer after stirring was stopped contained

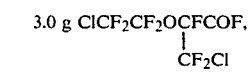

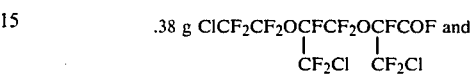

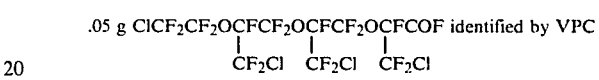

peaks at 1.00 min., 5.82 min. and 9.39 min. on 6 ft. $\frac{1}{8}''$ columns 20% Viton A on 80–100 mesh celite at 20 ml/min. carrier flow and temperature programmed at 4 min. at 60° C. to 220° C. at 16°/min. Mass spectroscopy confirmed the structures shown above.

EXAMPLE 2

50 ml dry tetraglyme and 4 g Na$_2$CO$_3$ were added to a 100 ml three-neck flask fitted with a stirrer, heating mantle, thermometer, an addition funnel and still head with a vacuum take off adapter with a collection vessel in a $-78°$ C. bath. A dry $N_2$ pad was used to maintain dry conditions prior to adding of the acid fluoride addition products. The acid fluoride addition product mixture from Example 1 containing 3 g n=0, 0.7 g n=1 and a small amount (0.1 g) n=2 acid fluorides was added dropwise to the stirring reactor mixture with accompanying evolution of gas. Following the completion of the addition, the reactor contents were stirred until no further gas evolution was observed at which time the heating mantle was turned on and the temperature in the vessel was raised slowly to 120° C. with a vacuum of 20 in. Hg applied. Further gas evolution was observed over the region of 60° C.–80° C. The reactor was cooled back down and 1.4 g of product was collected in the container, the VPC showed a peak at 0.59 min. which was identified as ClCF$_2$CF$_2$OCF=CF$_2$. The product has an I.R. band @ 1835 cm$^{-1}$ and a F$^{19}$ NMR spectrum consistant with the trifluorovinyl-oxo group.

EXAMPLE 3

Dry tetraglyme (25 ml) and 20.8 gms of CsF were added to a 200 ml, 3 neck flask equipped with magnetic stirrer, $-78°$ C. reflux condenser, thermometer and gas inlet tube. The contents were allowed to mix for 40 minutes.

The reactor contents were then cooled to 0°–5° C. and 25 gms of

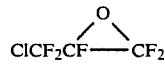

added slowly after which the contents were mixed for an additional 40 minutes. Another 25 gms of epoxide was then added in the same manner as described above. Two hours after the epoxide addition, with the contents at 0°–5° C., the product was distilled from the flask at 30 inches of vacuum while heating the flask up to 150° C. The maximum overhead temperature was 129° C. The product distilled in this manner (20.9 gms) was analyzed by VPC using the same column and program as described in the above examples.

| Peak time (min) | Wt. Ratio | Composition |
|---|---|---|
| 1.35 | 4 | ClCF$_2$CF$_2$CF$_2$OCFC(=O)F, with CF$_2$Cl branch |
| 6.79 | 2 | ClCF$_2$CF$_2$CF$_2$O(CFCF$_2$O(CF$_2$Cl))$_2$CFC(=O)F, with CF$_2$Cl branch |
| 9.86 | 1 | ClCF$_2$CF$_2$CF$_2$O(CFCF$_2$O(CF$_2$Cl))$_3$CFC(=O)F, with CF$_2$Cl branch |

EXAMPLE 4

17 g of a mixture containing 68%

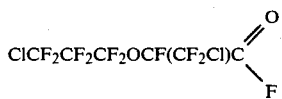

ClCF$_2$CF$_2$CF$_2$OCF(CF$_2$Cl)C(=O)F and higher homologs as analyzed by GC-mass spectrography was added dropwise to a stirred 3 neck reaction vessel containing 50 ml dried tetraglyme and 7.1 g dried Na$_2$CO$_3$ and fitted with a thermometer, heating mantle, and a stillhead with vacuum takeoff and double dry ice acetone trap under inert purge. Gas evolution was observed and a temperature rise from 25° C. up to 33° C. was observed during addition. After continued stirring for 1 hour, a 5 mm vacuum was applied and the temperature was raised slowly up to 100° C. in the vessel. Seven grams of material was collected in the primary collection receiver and identified as 97.1% ClCF$_2$CF$_2$CF$_2$OCF=CF$_2$. Raising the temperature under vacuum, up to 145° C., resulted in collection of an additional 2 g material which was analyzed by GC mass spectrography and I.R. as 22.35% ClCF$_2$CF$_2$CF$_2$OCF=CF$_2$ representing an 81% yield of ClCF$_2$CF$_2$CF$_2$OCF=CF$_2$. VPC analysis of the solvent in the reaction vessel showed some ClCF$_2$CF$_2$CF$_2$OCF=CF$_2$ remaining along with higher homologs.

COMPARATIVE EXAMPLE 4

A mixture (35 gms) containing 31.7% of

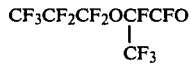

CF$_3$CF$_2$CF$_2$OCFCFO, with CF$_3$ branch plus higher homologs was added to a mixture of 15.5 gms Na$_2$CO$_3$ in 50 ml of tetraglyme at room temperature. After several hours and cessation of CO$_2$ evolution, the mixture was raised to 120° C. where upon there was indications of some slow CO$_2$ evolution. After several hours at this condition, pulling a vacuum on the system to remove product resulted in little or no evidence, by VPC and I.R., of vinyl ether formation. The temperature of the reactor was then raised to 160°–170° C. under atmospheric pressure. Under these conditions, boiling of the mixture resulted. The product collected (8 gms) showed a VPC peak at 0.74 min. retention time and absorption in the I.R. at 1840 cm$^{-1}$ indicating formation of the vinyl ether.

EXAMPLE 5

To a 100 ml 3 neck flask were added 50 ml of dry tetraglyme and 9.75 gms of anhydrous Na$_2$CO$_3$. The flask equipped with a stirring bar, reflux condenser, thermometer, and inlet port. Two, −78° C. cold traps in series were located downstream of the reflux condenser. A slight back pressure was maintained on the system with a dry N$_2$ bubbler. 15.95 gms of

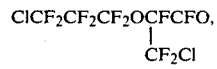

ClCF$_2$CF$_2$CF$_2$OCFCFO, with CF$_2$Cl branch were added slowly at room temperature. There was a small temperature rise, to about 35° C. and an evolution of CO$_2$, upon addition of the acid fluoride. The temperature was increased to 67°–68° C. and held there for 2.5 hours. The product was then distilled from the reactor. 12.59 gms of product was collected which analyzed 97.37% as ClCF$_2$CF$_2$CF$_2$OCF=CF$_2$. This gave a 0.60 minute peak on the VPC and represents a 99.3% yield to the vinyl ether.

The product was analyzed by IR and showed the —OCF=CF$_2$ at 1830 wave number.

Analysis of the product by F$^{19}$ NMR verified the ClCF$_2$CF$_2$CF$_2$OCF=CF$_2$ structure. A proton scan on the NMR showed only a negligible amount of proton containing material.

EXAMPLE 6

Tetraglyme (60 ml) and 7.5 grams of anhydrous Na$_2$CO$_3$ were added to a 100 ml 3 neck flask equipped with an air cooled reflux condenser, thermometer, magnetic stirrer and dropping funnel. Cold traps were located downstream of the reflux condenser. 20.9 grams of a mixture of acid fluorides consisting of 35.9%

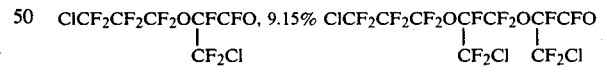

ClCF$_2$CF$_2$CF$_2$OCFCFO, 9.15% ClCF$_2$CF$_2$CF$_2$OCFCF$_2$OCFCFO, with CF$_2$Cl branches and higher homologs was added dropwise at room temperature. The temperature was maintained at no higher than 30° C. during the addition and until no further evolution of CO$_2$ occurred. The temperature was then raised to 70° C. and held there until no further evolution of CO$_2$. A 30 inch vacuum was then applied to the system and the pot temperature raised gradually to 142° C. while collecting the material boiling overhead. No appreciable CO$_2$ evolution ocurred during the distillation. 8.2 gms of material were collected that analyzed by VPC as

| Peak time (min) | Yield % | Composition |
|---|---|---|
| 0.67 | 31.9 | ClCF$_2$CF$_2$CF$_2$OCF=CF$_2$ |

-continued

| Peak time (min) | Yield % | Composition |
|---|---|---|
| 3.39 | 30.4 | ClCF$_2$CF$_2$CF$_2$OCFCF$_2$OCF=CF$_2$<br>                                       \|<br>                                    CF$_2$Cl |
| 5.98 | 3.9 | ClCF$_2$CF$_2$CF$_2$O(CFCF$_2$O\|CF$_2$Cl)$_2$CF=CF$_2$ |

The balance of the material being predominately solvent. Higher vinyl ether homologs remained in the flask.

EXAMPLE 7

An example of the polymerization of Cl(CF$_2$)$_3$—O—CF=CF$_2$ with fluorocarbon olefins is as follows: 3.7 g of Cl(CF$_2$)$_3$—O—CF=CF$_2$ was added to 400 ml deoxygenerated water containing 3 g K$_2$S$_2$O$_8$, 0.75 g NaHSO$_3$, 1.5 g Na$_2$HPO$_4$ and 3.5 g C$_7$F$_{15}$CO$_2$K under 60 psi applied tetrafluoroethylene pressure in a glass-lined stainless steel reactor with stirring at 20° C. After 2 hours, the reactor was vented and then is evacuated and heated to 50° C. to remove residual monomer. The reaction medium was then frozen, thawed, filtered and the polymer washed repeatedly and then vacuum dried 16 hours at 120° C. The polymer readily pressed into a flexible, tough, transparent film and analyzed to contain 3 percent chlorine.

EXAMPLE 8

As a further example of polymerization of Cl(CF$_2$)$_3$OCF=CF$_2$ with fluorocarbon olefins:

4.8 gms of Cl(CF$_2$)$_3$OCF=CF$_2$ were added to 30 ml of ClCF$_2$CFCl$_2$ in a stainless steel reactor. Two drops of a 2-tert. butylazo-2-cyano-4-methoxyl-4-methylpentane initiator solution were added and the reactor contents frozen to −78° C. The reactor overhead was evacuated and 21 gms of tetrafluoroethylene was condensed into the reactor. The reactor was heated to 55° C. and shaken for 16 hrs. After venting the reactor and evaporation of the solvent, 14 gms of dried polymer, analyzing as containing 2.36% Cl, was recovered.

What is claimed is:

1. A method of homopolymerizing one or more of the compounds represented by the general formula $$Y(CF_2)_a(CFR_f)_bCFR'_f{-}O{-}CF{=}CF_2$$

comprising reacting said compound in the presence of an initiator for a sufficient time and at a sufficient temperature to cause polymerization; where
  a=0 to 3;
  b=0 to 3;
  R'$_f$ and R$_f$ are independently selected from the group consisting of F, Cl, perfluoroalkyl radicals or fluorochloroalkyl radicals; and
  Y=Br.

2. The method of claim 1 where a=0–3, b=0–3 and R$_f$=R$_f'$=F.

3. The product produced by the method of claims 1 or 2.

4. A method of polymerizing one or more of the compounds represented by the general formula $$Y(CF_2)_a(CFR_f)_bCFR'_f{-}O{-}CF{=}CF_2$$

where
  a=0 to 3;
  b=0 to 3;
  R'$_f$ and R$_f$ are independently selected from the group consisting of F and Cl; and
  Y=Br;

and at least one other compound is selected from a second group of compounds selected from the group consisting of: trifluoromonochloroethylene, trifluoroethylene, vinylidene fluoride, 1,1-difluoro-2,2-dichloroethylene, 1,1-difluoro-2-chlorohexafluoropropylene, 1,1,3,3-pentafluoropropylene, octafluoroisobutylene ethylene, vinyl chloride, and alkyl vinyl ether; said method consisting essentially of reacting at least one compound from the first group with at least one compound from the second group in the presence of an initiator for a sufficient time and a sufficient temperature to polymerize said compounds.

5. The method of claim 4 where the compound selected from the second group is chlorotrifluoroethylene.

6. The method of claim 5 where a=0–3; b=0–3, and R$_f$=R$_f'$=F.

7. The product produced by the method of claim 4.
8. The product produced by the method of claim 5.
9. The product produced by the method of claim 6.

* * * * *

UNITED STATES PATENT AND TRADEMARK OFFICE
CERTIFICATE OF CORRECTION

PATENT NO. : 4,687,821

DATED : August 18, 1987

INVENTOR(S) : Bobby R. Ezzell, William P. Carl and William A. Mod

It is certified that error appears in the above—identified patent and that said Letters Patent is hereby corrected as shown below:

Col. 2, line 56; change "Fern" to --Fearn--.

Col. 3, line 44; change "expoxides" to --epoxides--.

Col. 7, line 18; change "interger" to --integer--.

Col. 8, line 17; change "interger" to --integer--.

Col. 15, line 23; change "deoxygenerated" to --deoxygenated--.

Under "ABSTRACT", 1st page; please insert the following paragraph after the 1st paragraph:

--These compounds may be decarboxylated to form useful monomers,

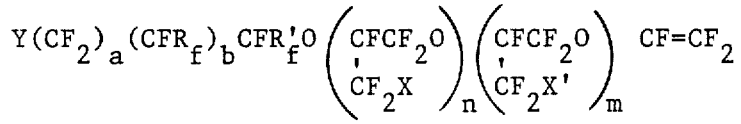

wherein
    a = 0 or an integer greater than 0;
    b = 0 or an integer greater than 0;
    c = 0 or 1;
    provided a + b + c ≠ 0;
    n = zero or an integer greater than zero;
    $R_f$ = F, perfluoroalkyl or fluorochloroalkyl;
    $X^f$ = F, Cl, Br or mixtures thereof when n>1;
    X' = Cl or Br;
    Y = Cl, Br, F or I;
    Z = F, OH, NRR' or OA;

UNITED STATES PATENT AND TRADEMARK OFFICE
CERTIFICATE OF CORRECTION

PATENT NO. : 4,687,821
DATED : August 18, 1987
INVENTOR(S) : Bobby R. Ezzell, William P. Carl and William A. Mod It is certified that error appears in the above-identified patent and that said Letters Patent is hereby corrected as shown below:

Continuation of paragraph of "ABSTRACT":

R and R' are independently selected from the group consisting of hydrogen, an alkyl having one or more than one carbon atom and an aryl;
A = alkali metal, quaternary ammonium, R or an aryl.

These monomers may then be polymerized into polymers having useful properties.--

Signed and Sealed this

Third Day of May, 1988

Attest:

DONALD J. QUIGG

Attesting Officer

Commissioner of Patents and Trademarks